United States Patent

Teitell et al.

[11] 4,013,474
[45] Mar. 22, 1977

[54] WOOD PRESERVATIVE COMPOSITIONS

[75] Inventors: Leonard Teitell; Sidney H. Ross, both of Philadelphia, Pa.

[73] Assignee: The United States of America as represented by the Secretary of the Army, Washington, D.C.

[22] Filed: May 6, 1975

[21] Appl. No.: 575,100

[52] U.S. Cl. .................... 106/2; 106/15 R; 106/287 SB; 424/347; 427/440

[51] Int. Cl.² .................... C09K 3/18; C09D 5/14

[58] Field of Search ............ 106/15 AF, 2, 287 SB; 424/347; 260/33.4 SB, 448.2 N; 427/440

[56] References Cited

UNITED STATES PATENTS

| | | | |
|---|---|---|---|
| 3,247,281 | 4/1966 | Gagliardi | 260/448.2 N |
| 3,600,408 | 8/1971 | Bursack et al. | 106/2 |
| 3,617,314 | 11/1971 | Hill | 106/15 AF |
| 3,794,736 | 2/1974 | Abbott et al. | 260/448.2 N |

*Primary Examiner*—Lorenzo B. Hayes
*Attorney, Agent, or Firm*—Nathan Edelberg; Robert P. Gibson; Arthur M. Suga

[57] ABSTRACT

Wood preservative, moisture-repellent and decay resistant compositions comprising pentachlorophenol and gamma-Aminopropyltriethoxysilane dissolved in major proportions of 2-butoxyethanol with a trace of water; and sodium pentachlorophenate with said silane in the presence of approximately equal proportions of water and 2-butoxyethanol.

2 Claims, No Drawings

WOOD PRESERVATIVE COMPOSITIONS

The invention described herein may be manufactured, used and licensed by or for the Government for governmental purposes without the payment to us of any royalty thereon.

This invention relates to the treatment of wood and more particularly concerns improved moisture-repellent compositions for preserving wooden ammunition boxes and the like which may be subjected to severe degrading environmental conditions.

Untreated wooden boxes, such as those used for ammunition packing, when exposed outdoors in a wet tropical climate will deteriorate in about 18 months. This finding was borne out during the recent Vietnamese conflict when large quantities of ammunition in wooden packing boxes were thus stored. As a result thereof, military specifications for wooden ammunition packing boxes were amended to require complete immersion thereof for a short period of time in a suitable wood preservative, which did substantially increase service life of these boxes in Vietnam, and prevented the spread of fungal attack from the infected wood to packaged items contained therewithin. Since the United States Army uses vast quantities of these boxes, it would be logistically and economically advantageous if lower cost treating solutions, providing good moisture repellency, wood preservation and decay resistance could be developed. Further, currently used wood preservatives require an undesirably prolonged drying period and thus oftentimes subjects packaged ammunition contained therewithin to damaging vapors.

It is accordingly an object of the present invention to provide compositions which dry readily, offer good moisture repellency, wood preservation and decay resistance.

This and further objects and advantages of the invention will be apparent as the description of the invention proceeds.

Briefly, we have discovered and developed silane-pentachlorophenate systems which form a reaction product which is capable of admirably preserving wooden ammunition containers even under severe degrading conditions. Silane-pentachlorophenol systems are also included in this invention.

More specifically, when sodium pentachlorophenate reacts with gamma-Aminopropyltriethoxysilane in the presence of substantially equal parts of water and 2-butoxyethanol, or when this silane is caused to react with pentachlorophenol in the presence of only a trace of water and major proportions of an organic solvent such as 2-butoxyethanol, biodeterioration of wooden berry boxes treated with the above formulations was admirably resisted.

The following examples are illustrative of our invention:

EXAMPLE I

| Compound | Organic Solvent System | |
|---|---|---|
| | Effective Range, parts by weight | Preferred Concentration, parts by weight |
| PCP* | 2.5 to 10.0 | 5.0 |
| Gamma-APTS** | 5.0 to 20.0 | 10.0 |
| Water | 0.2 to 1.0 | 0.5 |
| 2-Butoxyethanol | 92.3 to 61.0 | 84.5 |

*Pentachlorophenol
**Gamma-Aminopropyltriethoxysilane

EXAMPLE II

| Compound | Water & Organic Solvent System | |
|---|---|---|
| | Effective Range, parts by weight | Preferred Concentration parts by weight |
| NaPCP* | 2.5 to 10.0 | 5.0 |
| Gamma-APTS | 5.0 to 20.0 | 10.0 |
| Water | 40.0 – 52.5 | 42.5 |
| 2-Butoxyethanol | 40.0 – 52.5 | 42.5 |

*Sodium pentachlorophenate

The quantity of the PCP or NaPCP in the formulation will indicate the period of time that sawn veneer commercial wooden berry boxes, held together by metal staples, will resist decay by microorganisms. The preferred amount of 5 parts by weight of PCP or NaPCP has been found to offer good wood preservation when the boxes were subjected to various exposure tests. As expected, lesser concentrations of the PCP or NaPCP will protect the boxes a commensurately shorter period. An important consideration therefore is the balancing of the cost of the higher concentrations of the preservative against the desired number of years of preservation of the wooden ammunition boxes.

The silane should preferably be present in the formulations in approximately double the amount of the preservative (PCP or NaPCP). The function of the trace of water of Example I is to promote hydrolysis of the oxysilane. If below about 0.2 parts by weight of water is present, hydrolysis can be expected to be poor. If the water concentration is greater than about 1.0 part by weight, a tendency of the reaction product to gel up occurs and the resultant formulation considered to be of poor shelf life. In the water-organic solvent system of Example II, both NaPCP and the silane are water soluble and major proportions of both water and organic solvent are used. This water-based system, either as a solution or emulsion, substantially eliminates problems of residual hydrocarbons; is cheaper in cost; soaks into wooden boxes rapidly; emits less noxious vapors into the atmosphere; and reduces the fire hazard of treated berry boxes. We have found that a 1:1 ratio of water or organic solvent works well in preserving the berry boxes against deterioration.

An ambifunctional silane is employed in this invention. One portion of the gamma-APTS (hydrolysis products of ethoxy to form silanol groups) couples to the wood and the other portion (amino group) forms strong chemical bonds with the PCP or NaPCP, such that there effectively results a coupling between the preservative and the wooden substrate. It is not known for a certainty exactly at what position in the PCP or NaPCP molecule this strong chemical bonding occurs.

In Table I below, a standard wood preservative-water repellent used by the U.S. Army (Fed. Spec. TT-W-572B, dated 28 May 1969, with Amendment-1, dated 13 Apr. 1972) is compared with our formulations. The treated berry boxes were exposed above ground, and in soil contact, both at rain forest sites, Fort Sherman, Canal Zone, as well as in the "tropical chamber" at Frankford Arsenal, Philadelphia, PA. The boxes placed in this chamber were filled with biologically active soil and suspended with wire. Observations were made periodically to determine the condition of the boxes. Complete failure was reported when the boxes degraded to such an extent that the weight of the soil contained therewithin caused the box to fall apart and spill its contents.

The "Standard" used in the Table below comprised 5.0 parts by weight of PCP in a water repellent solution of:
 5 wt.% PCP (tech. grade)
 85 wt.% mineral spirits
 10 wt.% cosolvent:
  polypropylene glycol ether (m.w. 400–2000) 2 wt.%
  hydrogenated methyl ester of rosin 7 wt.%
  paraffin wax (m.p. 125°–130° C) 1 wt.%

The cosolvent enhances PCP solvency and prevents "blooming."

In Table I below, results of the "tropical chamber" laboratory tests and tropical exposure are presented. Preferred concentrations of the organic solvent system, and water + organic solvent system are those listed in Examples I and II respectively.

sion or soaking vessel, allowed to drain, and permitted to air dry for about 30 minutes. The boxes were then heat cured in a forced draft oven for about 10 to 30 minutes at about 95° to 105° C to effect polymerization and the formation of polysiloxane-fungicide complex. Dipping, spraying, painting, flooding etc. may also be used in applying our formulations to wooden boxes.

We claim:

1. A durable decay resistant preservative formulation for use with wooden products which must withstand severe tropical humidities in excess of 18 months, said formulation consisting of:
 5.0 parts by weight pentachlorophenol
 10.0 parts by weight gamma-aminopropyltriethoxysilane
 0.5 parts by weight water
 84.5 parts by weight 2-butoxyethanol

TABLE I

| Formulation | Decay of Veneer Boxes Impregnated with Preservatives | | | | | | |
|---|---|---|---|---|---|---|---|
| | Panama Exposure* | | | Tropical Chamber** | | | |
| | Soil Contact | Above Ground | | Lab. Soil Drop Test | | | |
| | 6 mos. | 6 mos. | 12 mos. | 9 mos. | 12 mos. | 15 mos. | 18 mos. |
| Standard | 5 | 3 | 5 | 0 | 3 | 4 | 5 |
| Org. Solvent System | 2 | 1 | 1–2 | 0 | 0 | 0 | 0 |
| Water + Org. Solv. System | 2–3 | 1 | 2 | 0 | 0 | 0 | 0 |

*Rating of decay is based on a scale of 0 to 5; 0 indicating no decay and 5 indicating destruction by decay. A trace, or suspicion of decay is indicated by a rating of 1; 2, slight, but definite, still serviceable; 3, moderate, but no more than small strength loss; 4, heavy, considerable strength loss and unserviceable.
**Values given indicate the number of boxes that decayed and faild at time periods stated.

In preparing our formulations, which may conveniently be accomplished at room temperature, the silane will be mixed with 2-butoxyethanol, and water added thereto. The PCP or NaPCP will then be dissolved thereinto.

In the actual treatment of the berry boxes, a simple 3 minute immersion soak was found to be most satisfactory. The boxes were then removed from the immersion 2. A durable decay resistant preservative for use with wooden products which must withstand severe tropical humidities in excess of 18 months, said composition consisting of, in parts by weight:
 5.0 Sodium pentachlorophenate
 10.0 Gamma-aminopropyltriethoxysilane
 42.5 Water
 42.5 2-Butoxyethanol

* * * * *